United States Patent [19]

Mitchell

[11] Patent Number: 4,937,457
[45] Date of Patent: Jun. 26, 1990

[54] PICOSECOND MULTI-HARMONIC FOURIER FLUOROMETER

[75] Inventor: George W. Mitchell, Sidney, Ill.

[73] Assignee: SLM Instruments, Inc., Urbana, Ill.

[21] Appl. No.: 309,251

[22] Filed: Feb. 10, 1989

[51] Int. Cl.$^5$ .......................... G01J 9/00; G01N 21/64
[52] U.S. Cl. ................................ 250/458.1; 356/317; 356/318; 356/417
[58] Field of Search ..................... 250/458.1; 356/317, 356/318, 417

[56] References Cited

U.S. PATENT DOCUMENTS

| | | | |
|---|---|---|---|
| 4,297,035 | 10/1981 | Bjorklund | 356/402 |
| 4,675,529 | 6/1987 | Kushida | 250/458.1 |
| 4,745,276 | 5/1988 | Broicher et al. | 250/458.1 X |
| 4,786,170 | 11/1988 | Groebler | 250/458.1 X |
| 4,840,485 | 6/1989 | Gratton | 250/458.1 X |

OTHER PUBLICATIONS

Fedderson et al., "Direct Waveform Collection and Analysis of Phase Fluorometer Data", *Biophysical Journal*, p. 401a, vol. 53, Feb. 1988.

Ramsey and Hietfje, "Signal-to-Noise Considerations in Fluctuation Analysis Spectroscopic Techniques", pp. 82-100, *American Society for Testing Materials*, 1983.

Bright et al., "Determination of Subnanosecond Fluorescence Lifetimes with a WHF Television Timer and a CW or Medelocked Laser", *Applied Spechoscopy*, vol. 40, No. 5, pp. 683-687, 1986.

Hieftje and Vogelstein, "A Linear Response Theory Approach to Time-Resolved Fluorometry", *Modern Fluorescence Spectroscopy*, Ch. 2, vol. 4, pp. 25-50, 1981.

Hietfje et al., "New Method for the Determination of Summenescence Lifetimes by Using the Beat Noise of a CW Laser as a Multi-Frequency Modulated Source", *Applied Physics Letters*, vol. 30, No. 9, pp. 463-466, May 1, 1977.

Haugen et al., "Stochastic Photolysis", *Applied Spectroscopy*, vol. 36, No. 3, pp. 203-209, 1982.

*Primary Examiner*—Constantine Hannaher
*Assistant Examiner*—J. Eisenberg
*Attorney, Agent, or Firm*—McCaleb, Lucas & Brugman

[57] ABSTRACT

A frequency domain spectrofluorometer employing extrinsically modulated DC light sources or intrinsically modulated laser pulse trains, containing multiple, harmonically related, phase-locked frequencies for exciting a fluorescent sample. High frequency light emissions of the excited sample are simultaneously cross-correlated with multiple, harmonically related, phase-locked R-F frequencies to produce workable low frequency electrical detector signals having the same phase and modulation characteristics as the multiple frequency sample light emissions. The detector signals are digitized in a computer and transformed from time to frequency domain by complex fast fourier transforms to extract the phase and modulation data for all frequencies of the sample light emissions. This data is displayed simultaneously on the visual presentation screen of the computer.

22 Claims, 11 Drawing Sheets

INSET A

MULTI FREQUENCY DATA AT SELECTED TIMES
EACH φM DATA SET = 1 POINT ON MAIN PLOT

FREQUENCY IN MHz VS PHASE φ MODULATION
TYPICAL nLLS CURVES FITTING
RESIDUALS FOR EACH DATA POINT

INSET B

LIFETIME KINETICS
QUENCHING OF
FLUORESCEIN FLUORESCENCE
BY K.I.
EACH POINT REPRESENTS
THE ANALYSIS OF A 5-85
MHz MULTI-FREQUENCY
DATA SET.

PICOSECOND MULTI-HARMONIC FOURIER FLUOROMETER

This invention relates to spectrofluorometers and more particularly to an improved type of frequency domain spectrofluorometer which is operable to acquire phase and modulation fluorescence lifetime data simultaneously at multiple frequencies of excitation.

Fluorescence emission from a fluorophore excited by a sinusoidal, amplitude modulated light is also sinusoidally modulated. However, the emission frequency is shifted and demodulated with respect to the phase and modulation of the exciting light by an amount related to the lifetime of the fluorophore's excited state. Instruments for measuring fluorescence lifetime by phase and modulation techniques are known as phase or frequency domain fluorometers.

According to heretofore known practice, frequency domain fluorescence lifetime analysis is dependant on the acquisition of high resolution phase shift and demodulation values of a test sample's emission at a number of single frequencies of excitation. Typically, in practice, a dozen or more measurements are required at different excitation frequencies in order to adequately define a sample's response curve. Consequently, inasmuch as all known current phase/modulation fluorometers operate at selected single detection frequencies, the construction of a sample's response curve is not only tedious, but time consuming-usually requiring one-half to one and one-half hours to complete.

The present invention overcomes the aforedescribed difficulty by capturing the excited fluorophore's response curve in a single measurement through simultaneous acquisition of phase and modulation data at multiple frequencies. This capability affords acquisition of the samples response curve in a matter of seconds rather than hours.

BRIEF DESCRIPTION OF THE INVENTION

In brief, this invention comprises a cross-correlation, frequency domain spectrofluorometer operable to measure simultaneously the phase and modulation responses of a fluorescent sample at multiple frequencies of excitation. Amplitude modulated light is produced from extrinsically modulated D.C. light sources or intrinsically modulated laser pulse trains containing multiple, harmonically related, phase-locked frequencies for exciting the sample. Means are provided for detecting and cross-correlating test sample emission signals and radio frequency signals simultaneously at the multiple harmonically related frequencies thereof to provide detector signals having the phase and modulation characteristics of the emission signals. Additional means serve to extract the phase and modulation data of each individual frequency of the detector signal for analysis and visual presentation in the form of frequency response curves, excited state reactions, dynamic rotational rates or energy transfer curves of the test sample.

It is an important object of this invention to provide a new class of frequency domain fluorometer which is operable to measure the phase and modulation responses of an excited fluorescent sample simultaneously at multiple frequencies.

It is another important object of this invention to provide a fluorometer of the order set out in the preceding object which employs cross-correlation detection and fourier transform techniques.

It is another object of this invention to provide a frequency domain fluorometer capable of capturing the frequency response curves, excited state reactions, dynamic rotational rates or energy transfer curves of a fluorescent sample in a single measurement which fully satisfies the requirements of lifetime analysis and which is obtained at millisecond time intervals for kinetic recording.

It is still another object of this invention to provide a frequency domain fluorometer which is capable of exciting a sample fluorophore and detecting its emission response simultaneously and at multiple frequencies of excitation.

Another important object of this invention is to provide a frequency domain fluorometer which employs amplitude modulated light from DC light sources containing multiple harmonically related, phase-locked frequencies used for exciting the sample fluorophore.

A still further object of this invention is to provide a fluorometer employing any collimated incoherent light source, a CW laser, a synchronously pumped dye laser or any intrinsically modulated coherent or incoherent light source for exciting the test sample.

A further important object of this invention is to provide a multi-harmonic, fourier fluorometer for collecting phase/modulation lifetime data simultaneously at multiple frequencies of excitation.

Another important object of this invention is to provide a fluorometer of the nature set out in the next preceding object which employs phase coherent, harmonic generators and photomultipliers which simultaneously cross-correlate and detect high-frequency phase and amplitude information at a fundamental frequency and its integer harmonics.

Having described this invention, the above and further objects, features and advantages thereof will appear from the following detailed description of preferred and modified embodiments thereof, illustrated in the accompanying drawings and representative of the best mode presently contemplated for carrying out its concepts and teachings so as to enable one of skill in the art to practice this invention.

In order to facilitate understanding of the features and scope of this invention, two implementations of the fluorometer will be described; one employing an inexpensive CW laser as the light source and one using a synchronously pumped dye laser for that purpose. The two instruments differ principally in the fact that the dye laser source is inherently modulated whereas the CW laser requires external modulation.

DESCRIPTION OF THE PREFERRED EMBODIMENT

Figure 1:
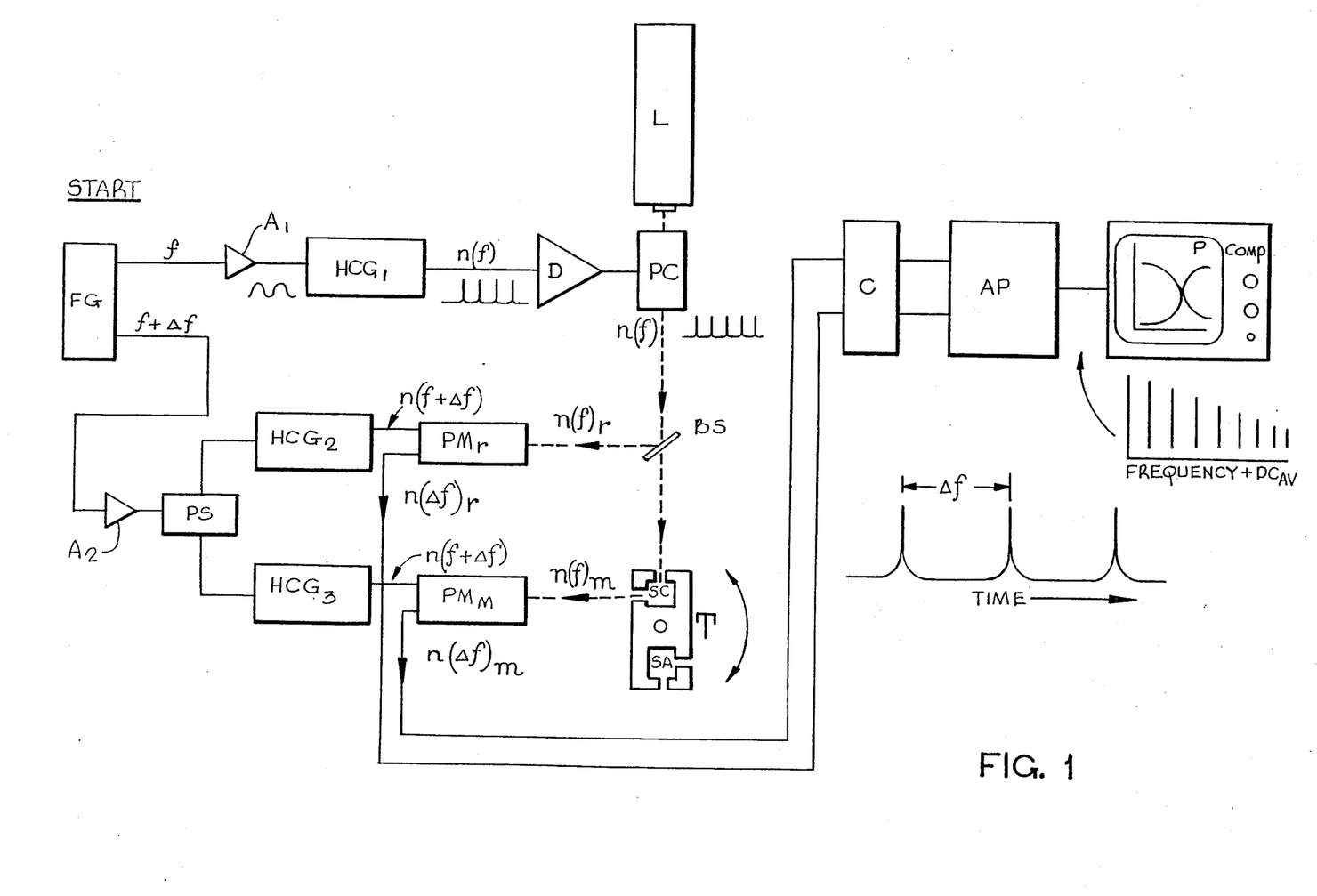
FIG. 1 is a schematic block diagram of a frequency domain fluorometer employing a CW laser light source in accordance with this invention.

With initial reference to FIG. 1 of the drawings, a block diagram of a preferred form of fluorometer according to this invention is set forth to illustrate the fundamental or the basic components of a multi-harmonic fourier transform fluorometer employing a continuous wave (CW) laser as a light source (L). Any collimated, coherent or incoherent DC light source may be substituted for the CW laser.

As there shown, a frequency generator (FG) generates a pair of phase locked sinusoidal radio frequencies (f) and (f+Δf). For illustration purposes, the fundamental frequency (f) may be considered to have a value of 5 MHz and the second frequency (f+Δf) a value of 5 MHz plus 3 Hz. The fundamental 5 MHz frequency is fed to a buffer amplifier (A1) and serves to drive a harmonic comb generator (HCG-1) whose output contains all integer harmonics of the 5 MHz fundamental frequency i.e., (5, 10, 15, 20, 25 ... MHz). This signal is used to modulate the intensity of the CW laser (L) via a pockels cell (PC) and its associated driver (D). The modulated laser output contains the 5 MHz fundamental frequency (f) and its harmonics and is utilized to excite samples located in a rotatable turret (T) which carries a zero lifetime solution (SC) and a test sample fluorophore (SA). The turret (T) may be manually indexed or power driven according to known practice.

The secondary frequency output signal (f+Δf) of the frequency generator (FG), i.e. 5 MHz plus 3 Hz, is amplified by (A2) and fed to a power splitter (PS) which produces a pair of equal strength signals that are used to drive a pair of harmonic comb generators (HCG-2 and HCG-3). The outputs of the comb generators contain the fundamental and harmonic frequencies of N(f+Δf) i.e., 5 MHz plus 3 Hz, 10 MHz plug 6 Hz, 15 MHz plus 9 Hz ... etc. These generator output signals are utilized to modulate the gain of two photomultiplier detectors (PMr and PMm), as will now be described.

Reference photomultiplier (PMr) receives a small portion (approximately 3%) of the intensity modulated, exciting light signal $N(f)_r$ from the CW laser via a beam splitter (BS). This signal is cross-correlated with the input signal N(f+Δf) from the comb generator (HCG-2), by hetrodyning or mixing the harmonics of the two signals to produce a low frequency beat note or reference signal $N(\Delta f)_r$ which has a repetition rate equal to the difference between the mixed signals; in this case 3 Hz.

In a similar fashion the measuring photomultiplier (PMm) detects the signals $N(f)_m$ from either the scattering (zero lifetime) solution (SC) or the test sample (SA), (which it observes alternately) and mixes the harmonics of such detected signals with the respective harmonics of the gain modulating signal N(f+Δf) input from HCG3. This produces a low frequency beat note $N(\Delta f)_m$ having a repetition rate equal to the difference between the frequency pair created by generator (FG), i.e., 3 Hz. This signal contains the cross-correlated phase and demodulation information for all the radio frequency harmonics. Thus the 3 Hz component of the photomultiplier tube output signal contains the information for 5 MHz; the 6 Hz component, the information for 10 MHz; the 9 Hz component, the information for 15 MHz ... and so forth.

The output signals from the photomultipliers (PMr) and (PMm) are fed to a computer (C) which digitizes and stores the signals which are then transformed into the frequency domain by means of an array processor (AP) that performs complex fast fourier transforms on the data. This latter operation results in arrays of real and imaginary values used to calculate the amplitudes and phases of the time domain wave which is transformed into frequency domain.

The array processor also implements a mathematical low pass filter which produces the average DC values of the photomultiplier signals (DC av). Phases and amplitudes for the harmonics are extracted from the fourier transforms by conventional operations.

The results are visually displayed on the screen of a personal computer in the form of response curves (phase and amplitude vs. frequency) for the test sample (SA).

In order to measure a test sample the following general procedure is employed:

The turret (T) is positioned so that (PMm) is observing the zero lifetime scattering solution (SC). Under these conditions the amplitudes of the (PMm) harmonics divided by the common (DC av) value creates a set of normalizing modulation values which are stored for later use, as will appear presently.

Phase angles are computed and set to a common reference by taking the phase differences between the harmonics of the reference photomultiplier (PMr) signals and the respective harmonics of the measuring photomultiplier (PMm) signals when observing the scattering solution (SC). For example, assume that this difference is 20° at the frequency for harmonic (n). Corresponding differences are measured for each of the harmonic frequencies and these measurements create a set of normalizing phases which are analogous to the set of reference or normalizing modulation values.

The turret is next positioned so that (PMm) is observing the sample (SA). The amplitudes of the (PMm) harmonics are measured, their modulations calculated by ratioing them against their common (DC av) value and those values are normalized by ratioing them against the corresponding normalizing modulation values previously noted. This creates a set of sample demodulations for the harmonics of the measured sample (SA).

A set of sample phase shifts for the measuring photomultiplier (PMm) harmonics is obtained by subtracting the normalizing phases from the measurement phases.

A plot and printout of phase shifts and demodulations vs. frequency of excitation constitute the basic output of the instrument which is presented as a sample response curve visually presented on the personal computer screen. Noise may be reduced by repetitive, interleaved measurements of the scatter and sample observations and averaging of the phase shifts and demodulations.

The response curves set out in FIGS. 2-6 are examples of data produced by a fluorometer instrument in accordance with this invention and demonstrate the comparative ability thereof to accurately resolve single and multi-component lifetimes as well as dynamic rotational rates on samples of well known characteristics.

Figure 2:
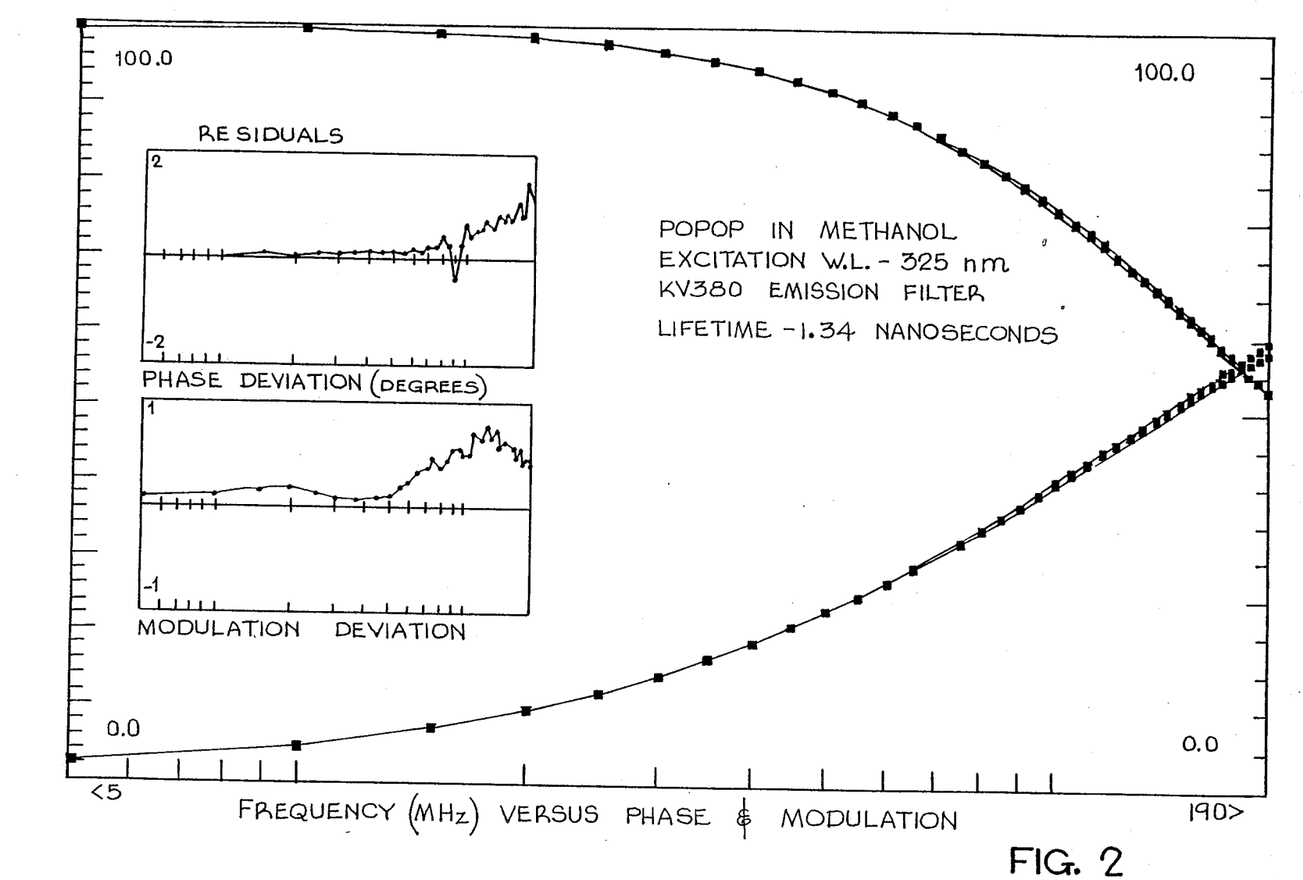
FIGS. 2-6, are sample phase shift and demodulation response curves for samples of known characteristics.

FIG. 2 graphically illustrates simultaneous multifrequency phase shift and demodulation measurements for the organic scintillator, POPOP, p-bis [2-(5-phenyloxazolyl) benzene] dissolved in methyl alcohol. Literature values of the fluorescence lifetime for POPOP range from 1.32 to 1.369 nanoseconds. Non-linear least squares fitting of the instrument's measured data to a single exponential decay model recovered a lifetime for POPOP of 1.34 nanoseconds.

Figure 3:
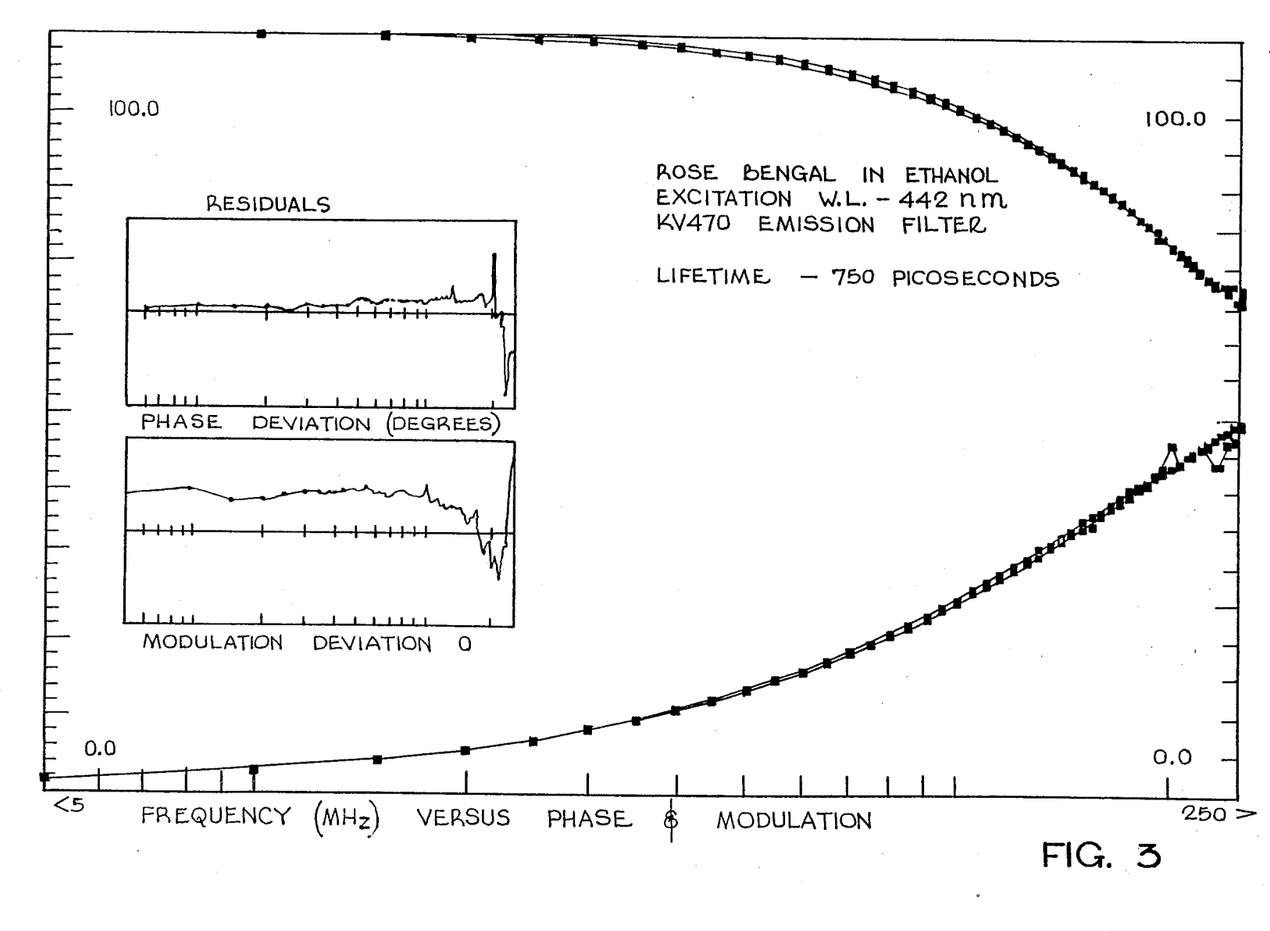

FIG. 3 graphs simultaneous multifrequency phase shift and demodulation measurements for the organic dye, rose bengal dissolved in ethyl alcohol. Literature values for the fluorescence lifetime of rose bengal range from 500 to 830 picoseconds. Non-linear least squares fitting of the measured data to a single exponential decay model recovered a lifetime for rose bengal of 750 picoseconds.

Figure 4:
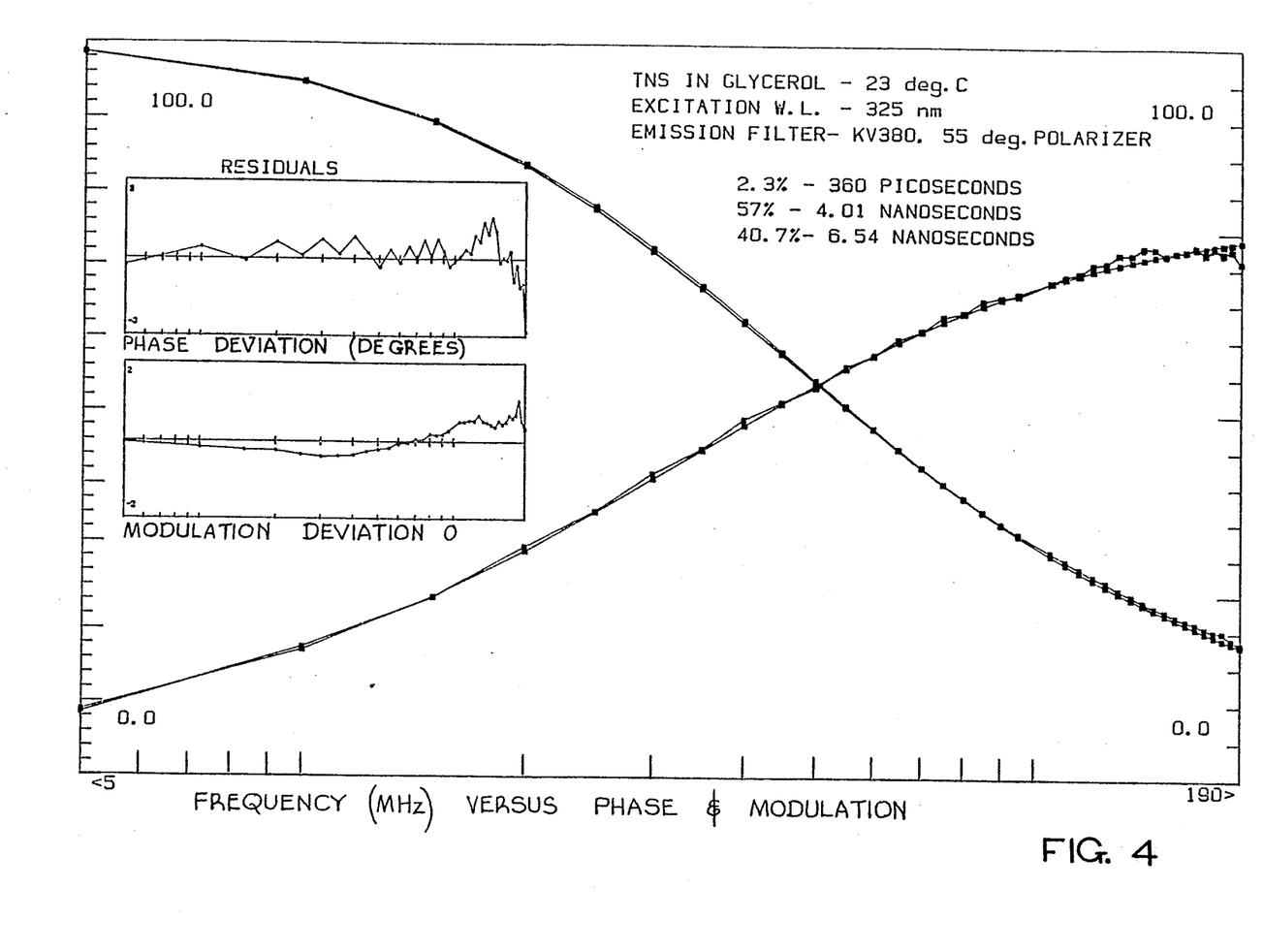

A demonstration of the ability of the fluorometer of this invention to resolve multiple lifetime components in a fluorescent sample is set out in FIG. 4. The molecule TNS, 2-p-Toluidinyl-6-napthalenesulfonic acid, undergoes solvent relaxation which results in the observation of multiple decay rates. Non-linear least squares fitting of the measured data to a 3 decay model recovered: 2.3% of the decay at 360 picoseconds; 57% of the decay at 4.01 nanoseconds and 40.7% at 6.54 nanoseconds. This result is consistent with values reported in the literature.

Figure 5:
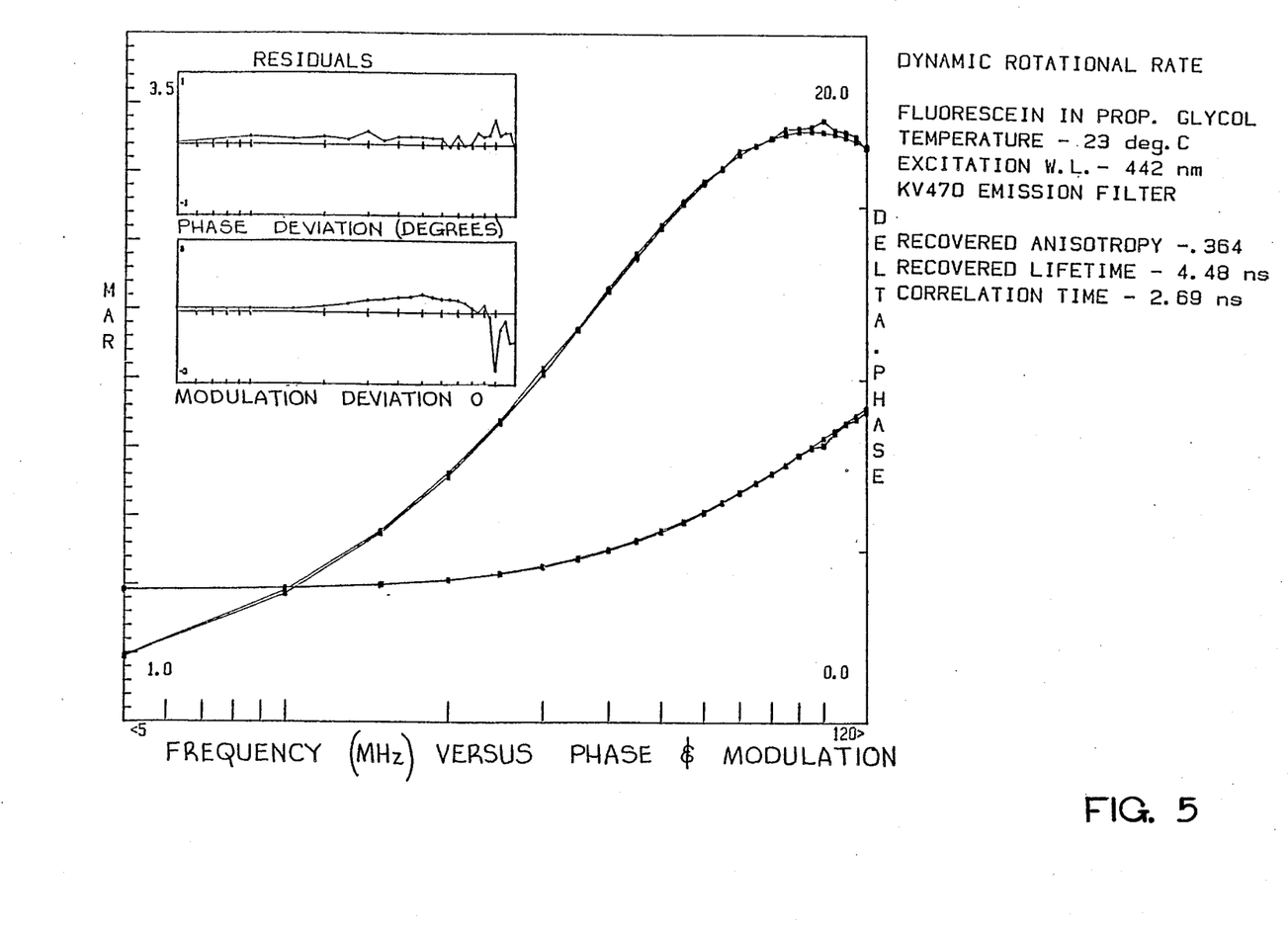

Simultaneous multifrequency measurements of the differential polarized phase and ratio of the modulated amplitudes in order to recover the dynamic rotational rate of the molecule fluorescein dissolved in propylene glycol is shown in FIG. 5. Non-linear least squares fitting of the measured data to a single rotational rate (isotropic)-single decay model recovered a rotational correlation time of 2.7 nanoseconds; a decay rate of 4.48 nanoseconds and a limiting anisotropy of 0.364. Comparable values are reported in the literature.

Figure 6:
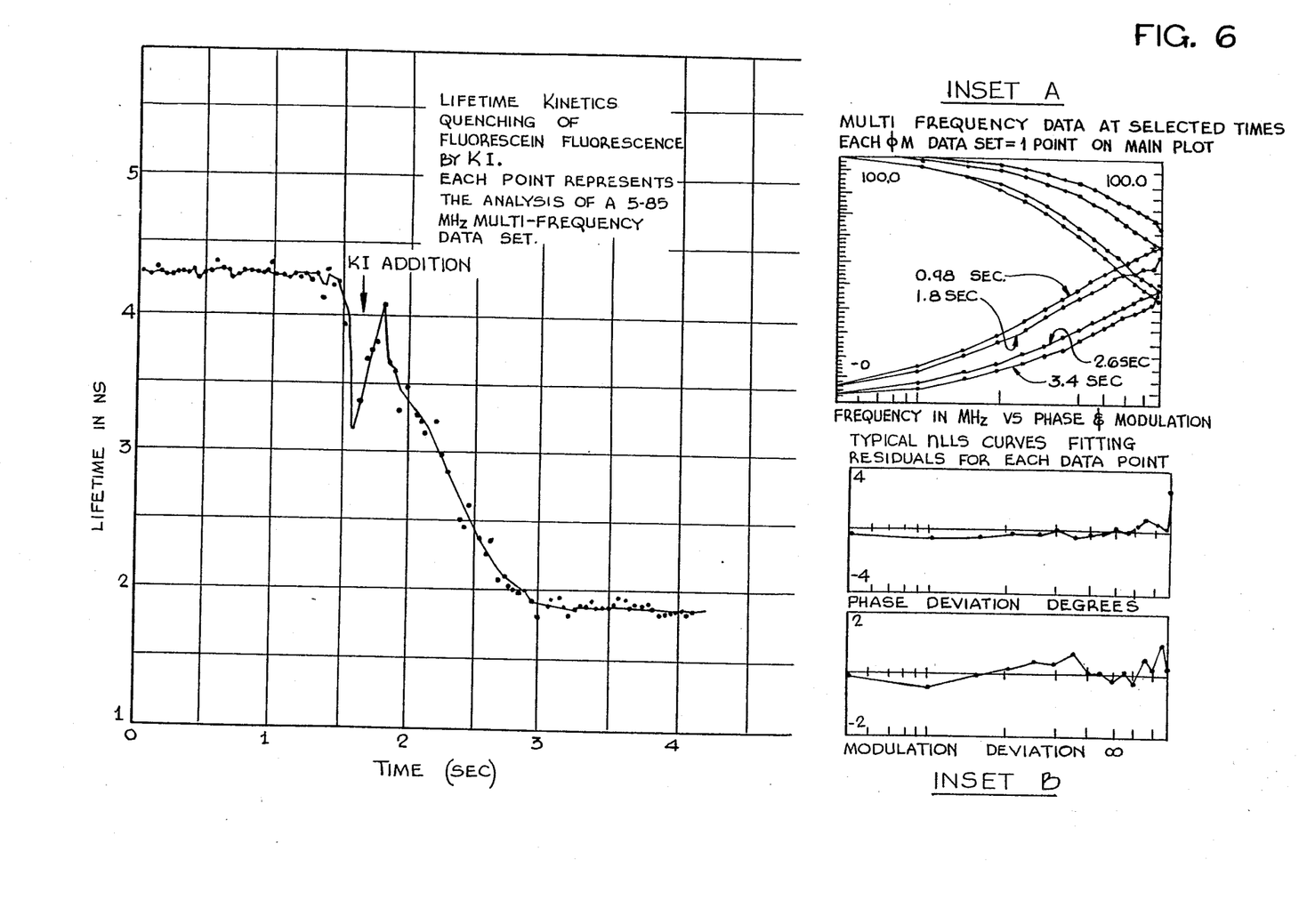

FIG. 6 demonstrates the kinetics measuring capability of the fluorometer of this invention. The inorganic salt, potassium iodide (KI) is a quencher of fluorescence emission causing a decrease in emission intensity and a shortening of the fluorescence lifetime. The instrument was set to make a multifrequency phase/modulation measurement every 33 milliseconds and observe the emission from a solution of fluorescein in 0.1 N sodium Hydroxide contained in a stirred cuvette. Twenty (20) microliters of a concentrated solution of KI was injected into the cuvette at a point on the figure notated "KI addition".

The fluorometer clearly resolved the time course of fluorescein/KI mixing as a decrease in fluorescence lifetime from 4.3 nanoseconds to a final value of 1.8–1.9 nanoseconds. Each point on the main graph represents the analysis of a simultaneous multifrequency data set from the fluorometer. Typical data sets at various times and their residual "goodness of fit" to the model are shown in insets A and B, respectively. Complete frequency response curves were acquired every 30 milliseconds.

IMPLEMENTATION

The implementation of a multi-harmonic fourier fluorometer in accordance with the teachings of this invention is graphically illustrated by the schematic circuit diagram shown in FIG. 7 (Parts 7C–7E) of the drawings.

As there set out, (FIG. 7C) a direct frequency synthesizer 20 is used as the frequency source or generator; (FG of FIG. 1). A synthesizer for this purpose is commercially available from Programmed Test Sources, Inc. of Littletown, Mass., Model PTS-250. The 10 MHz reference oscillator output of the PTS-250 is capacitively coupled to the clock input of a transistor-transistor logic (TTL), J-K flip-flop 21 with appropriate level shifting, or resistor network, on the clock input, necessary to trigger the flip-flop to toggle and divide the 10 MHz input frequency in half, i.e., 5 MHz. Model 74S112 TTL Schottky flip-flop is available for this purpose from Texas Instruments, Inc., Dallas, Tex. Since the output (Q) of the flip-flop 21 is a square wave, it is passed through a low pass filter 22 (PLP-10.7, Mini-Circuits Laboratory, Brooklyn, N.Y.) which removes the harmonics of the 5 MHz fundamental frequency.

Figure 7A:
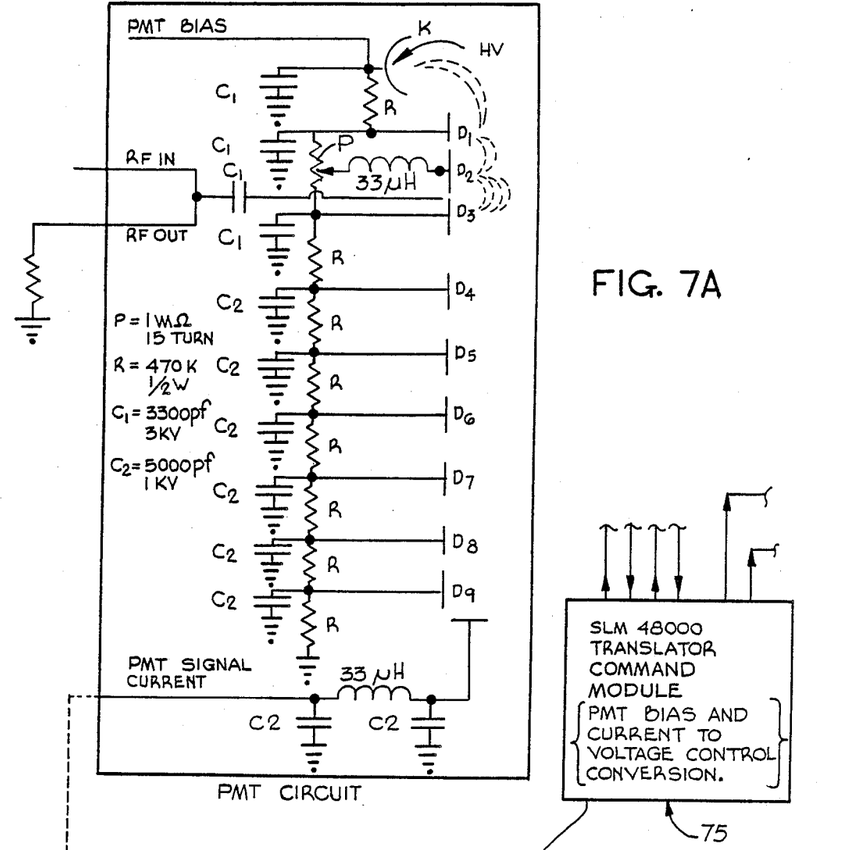
FIGS. 7A and 7B are subcircuit diagrams of the FIG. 7 schematic circuit.
Figure 7B:
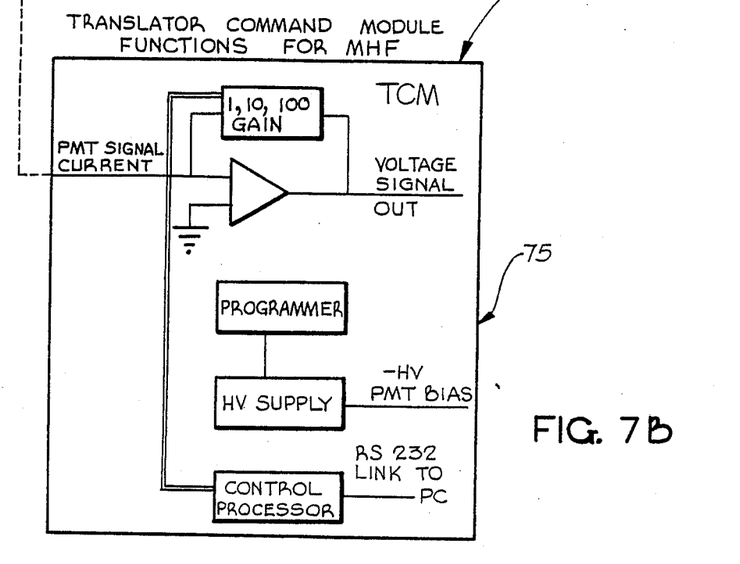
Figure 7C:
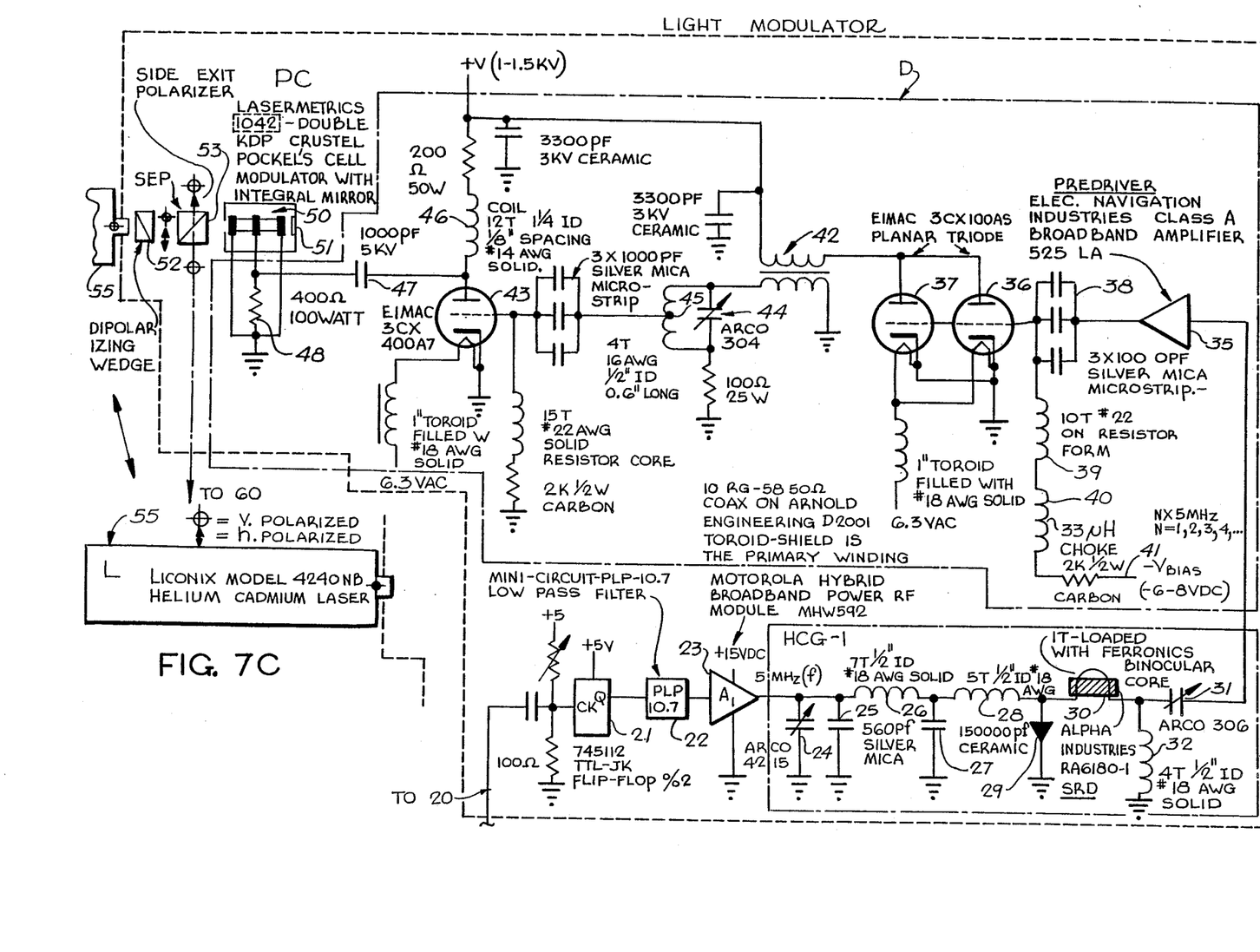
FIG. 7 (broken into parts 7C-7E) is a schematic diagram of the circuitry employed for implementing a fluorometer of the order illustrated in FIG. 1.

The 5 MHz output of filter 22 is fed to a hybrid amplifier 23 (Model MHW-592 Motorola, Inc. Semi-Conductor Products, Phoenix, Ariz.) and boosted to approximately 1 watt after which it is impedance matched to a first impulse network comprising a variable capacitor 24 (Arco Electronics, Chatsworth, Calif. Model 4215); a 560 pf silver mica capacitor 25; a seven turn, one-half inch, I.D. inductance 26; and a 5,000 pf ceramic capacitor 27. This impedance matching network feeds an impulse generator network composed of a five turn, one-half inch ID storage coil 28 and a step recovery diode (SRD) 29 (Alpha Industries, Woburn, Mass., Model RA 6180-1). The impulse network comprising the coil 28 and SRD 29 is rematched to 50 ohms by high-pass filtering using an output network comprising a single turn hairpin loaded with a binocular core indicated at 30; a variable capacitor 31 and an impedance 32, formed as a four turn one-half inch ID coil. The impedance matching, impulse circuit and the output circuit comprising items 24–32 constitute the comb generator HCG-1 of FIG. 1.

Inasmuch as success of a multi-harmonic fluorometer in accordance with this invention is largely dependent on a circuit which generates an output consisting of many integer harmonics of a single input frequency, the workings of the harmonic comb generator circuit just described is primary to an understanding of this invention.

In accordance with the embodiment illustrated in FIG. 7C, the important comb generator function is carried out by appropriate operation of a special semiconductor, step recovery diode SRD indicated at 29. Under the parameters of the FIG. 7C circuit, it is necessary that SRD 29 be capable of working at a low input frequency, in this case 5 MHz, supplied by the bi-polar sinewave frequency produced by amplifier 23 which is impedance matched to the inductance/SRD combination to form the impulse generator. More specifically, amplifier 23 supplies one to one and one-half watt sinewave input power and its 50 ohm output is matched to the impulse circuit impedance (item 28) by an adjustable pi network comprising items 24–27, of the described circuit. Output network (items 30–32) combines impedance matching back to 50 ohms with a simple high pass filter to reject the fundamental sinewave feed-through from amplifier 23. During the positive part of the input cycle, the SRD 29 conducts current, building minority carriers and storing charge in coil 28. The diode continues to conduct for a short period (delay time) after the input swings negative due to the presence of the minority carriers. When the carriers are depleted, the diode suddenly stops conducting current and energy stored in coil 28 is transferred to the load as an impulse which contains integer harmonics of the input frequency up to a limit determined by the transition time of the diode. Spectrum analysis of the output appears as an envelope of evenly spaced frequencies and hence the name "comb" or "picket fence" generator.

In the illustrated circuit of FIG. 7C the output of the harmonic comb generator HCG-1 is fed to a pre-driving amplifier 35 of the pockel's cell driver (D in FIG. 1) where it is pre-amplified to approximately +80 volts peak. Amplifier 35 in the illustrated circuit constitutes an ultra-linear, 1–500 MHz broadband amplifier, (commercially available as Model 525LA Broad Band, 25 watt, class A amplifier, ENI Power Systems, Rochester, N.Y.). The pre-amplified impulse emanating from amplifier 35 contains the 5 MHz fundamental frequency and all of its integer harmonic frequencies, up to approximately 350 MHz.

The output generated by the pre-driving amplifier 35 is capacitively coupled to the grids of a pair of planar triodes 36 and 37 (3CX100A5, Varian Eimac, Salt Lake City, Utah) over a capacitor network 38, comprising three 1000 pf silver mica capacitors. The triodes are normally kept from conducting by the application of a small negative bias voltage ($-V$ bias) of 6 to 8 volts DC, by means of a resistor-inductor network 39, 40 and 41. The application of the driving impulse from 35 causes the tubes 36 and 37 to conduct heavily. The plate current passes through an inverting transformer 42, formed in this instance from a 10" length of coaxial cable (10T, RG58, 50 ohms) loaded with a high frequency ferrite toroid (Arnold Engineering Co., Marengo, Ill.). The amplified impulse from transformer 42 is capacitively coupled to the grid of a final stage triode 43 (3CX400A7, Varian Eimac) through a "bridged-T" network having a variable capacitor 44 and a center tap, four turn ½-inch I.D., 0.6 inch long coil 45 adjusted to cancel the grid capacitance of the triode 43.

The final stage triode 43 is a zero-bias triode which is normally non-conducting until the arrival of an impulse at its grid which causes it to suddenly conduct and transfer energy stored in inductor 46 through capacitor 47 to an ultra-low inductance, resistive load 48, while impressing a voltage transient on the center terminal of a double crystalline pockel's effect, electro-optic light modulator 50, having an integral back reflecting mirror 51 (Lasermetrics 1042). This activity conditions the pockel's cell to pass a pulse of harmonically modulated light, as will be amplified hereinafter.

After inductor 46 is discharged it isolates the triode 43 from the power source (+v 1–1.5 kv) and then recharges for the next pulse. The pockel's cell pulse driver circuit or amplifier described (items 35–48 and related circuit components) can deliver peak power levels of at least 3,000 watts at high repetition rates and with harmonic phase coherence. This circuit arrangement is also relatively inexpensive, compact and very rugged and dependable in operation.

It will be noted that the pockel's cell 50 is coupled to an optic system comprising a depolarizing quartz wedge 52 and a side exit polarizer 53 arranged to transmit polarized light to the pockel's cell in response to operation of the CW light source 55 (L of FIG. 1) which in this case may be a commercially available helium-cadmium laser (Model 4240NB from Liconix, Inc. of Sunnyvale, Calif.). The laser 55 is operable to provide CW light at 325 or 442 nanometers as input to the pockel's cell light modulator.

As indicated in FIG. 7C, the light source 55 produces a vertically oriented polarized output (crossed circle symbol) which passes through the depolarizing quartz wedge 52 and enters a side exit calcite polarizer 53. This polarizer rejects vertically polarized light and allows horizontally polarized light, as indicated by the vertical double ended arrow symbol, to pass into the light modulating pockel's cell 50. The latter cell operably rotates the electric vector of the horizontal polarized light toward the vertical; rotating the same to a degree which is proportional to the electric field generated by the initiating impulse received from the driver circuit (D of FIG. 1).

A back mirror 51 of the pockel's cell modulator reflects the laser beam light through the KDP crystals of the pockel's cell where the polarization undergoes further rotation and reenters the side exit polarizer 53 which reflects the vertical component of the polarized light laterally and directs the same into an optical module 60, (see FIG. 7E) such as an Model OP-450, available from SLM Instruments, Inc., Urbana, Ill.

Upon entering module 60 the polarized light excites the appropriate sample (SC or SA) in the turret 61 (T) after passing through beam splitter 62 (BS), the latter of which reflects a portion of the light signal (approximately 3%) to the reference photo tube (PMr) indicated at 63. The remaining light which passes through the sample in turret 61 enters the measuring photo tube 64 (PMm) via filter 65.

In brief summary of the foregoing operation, it is to be noted that no light will be present at the sample in turret 61 until the arrival of an electric impulse at the center terminal of the pockel's cell 50. Such impulse generates an electric field across a pair of electro-optic crystals of the pockel's cell which rotate the electric vector of the input light in a direction that causes the light to reflect out the side of the calcite polarizer 53 and onto the sample (SA) or (SC) in the turret 61 (T). The light applied to the sample is therefore an intensity modulated replica of the electrical impulse and as such contains the fundamental 5 MHz and its integer harmonics up to a practical limit dictated primarily by the frequency response of the particular pockel's cell (250 MHz in this circuit example).

Figure 7D:
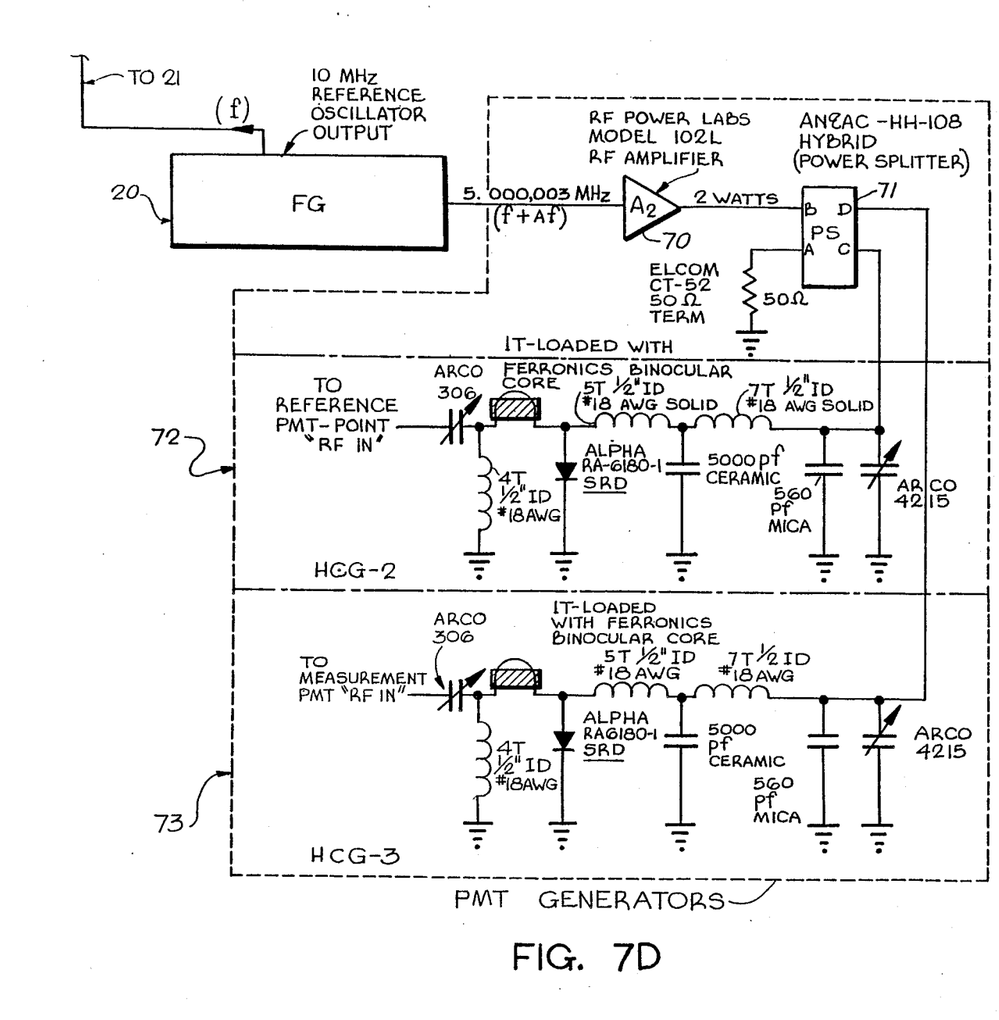
Figure 7E:
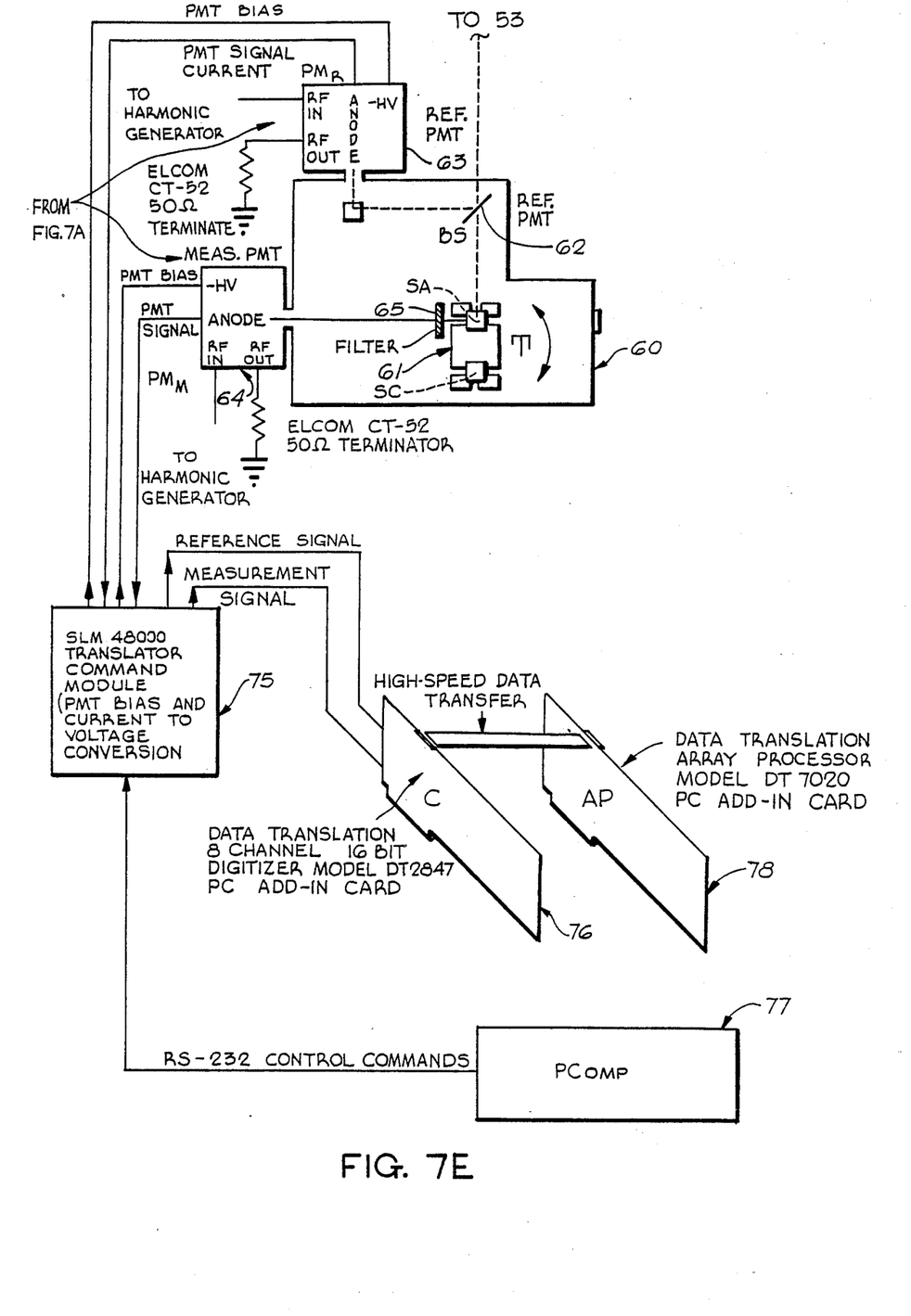

Turning now to the operation of the photomultiplier cross correlating generators, attention is again directed to the synthesizer or frequency generator 20 (FG) of FIG. 7D which is set to produce a main frequency output of 5.000,003 MHz, in the case herein of illustration. This frequency corresponds to $(f+\Delta f)$ of the FIG. 1 illustration and is amplified to 2 watts by a radio frequency amplifier 70 ($A_2$) for which purpose a broad band RF, amplifier Model 102L is available from RF Power Labs, Inc., Bothell, Wash. The 2 watt output of amplifier 70 is fed to a power splitter 71 (PS), such as a commercially available Model HH-108 hybrid power splitter from Adams Russell - Anzac Division, Burlington, Mass. Power splitter 71 divides the 2 watt signal equally in order to drive a pair of impulse generators 72 and 73 which correspond to the generators (HCG-2) and (HCG-3) of the FIG. 1 illustration. Inasmuch as these generators are identical to the above described (HCG-1) generator used for the light modulator, no further description thereof is deemed necessary.

The outputs of the two generators 72 and 73 will be 5.000,003 MHz and it's integer harmonics up to approximately 350 MHz. Outputs of the two generators HCG-2 and HCG-3 are fed to the photomultiplier tubes 63 (PMr) and 64 (PMm), respectively, and serve to modulate the gain of such tubes by varying the voltage bias of their second dynode $D_2$ (see the subcircuit FIG. 7A, labeled PMT Circuit). It will be understood in this respect that each of the photomultiplier tubes 63 and 64 has a circuit in accordance with FIG. 7A. The second dynode $D_2$ of each of the photomultiplier tubes is biased by a potentiometer (P) so that the gain of the photomultiplier tube is low in the absence of an impulse from it's generator. An impulse received from a generator (HCG-2) or (HCG-3) to its respective photomultiplier tube 63 or 64, as the case may be, serves to increase the gain of the photomultiplier tube approximately 10 fold.

The photomultipliers observe harmonically modulated light and simultaneously are gain modulated by a comb of phase-locked harmonics, offset from the modulated light signal by ($\Delta f$), which in this illustrated case is 3 Hz. In this latter regard the 3 Hz value is arbitrary and in kinetic operation the ($\Delta f$) is selected at 100-300 Hz in order to increase time resolution for that mode of operation of the described fluorometer of this invention.

The light impulse and gain impulse are mixed in the photomultiplier tubes at dynode $D_2$, creating a beat note at a 3 Hz repetition rate which contains simultaneously the phase and amplitude information for all detected radio frequency harmonics, viz. 3 Hz=5 MHz; 6 Hz=10 MHz; 9 Hz=15 MHz and so on, up to a limit for this specific instrument of about 250 MHz. The beat note emanating from dynode $D_2$ is amplified by $D_3$ and succeeding dynodes $D_4$-$D_9$ to produce a photocurrent which is sent to a command module (see sub FIG. 7B) indicated generally by 75. In this instance, the command module illustrated is of a type commercially available as an SLM 48000 Translator Command Module, SLM Instruments, Inc., Urbana, Ill. (see FIG. 7E).

The command module provides high voltage bias for the photomultipliers 63 and 64 and converts the photocurrents received from the photomultiplier tubes into proportional voltage outputs which serve as inputs for a high speed, high accuracy digitizer 76 (Model DT2847 Data Translation, Inc., Marlboro, Mass.) comprising a circuit board resident in a personal computer 77 marked (PCOMP) in FIG. 7E. In practice a commercially available Model PC-286, Dell Computer Company, Austin, Tex. has been employed for the computer 77.

The photomultiplier tube wave forms are digitized and contain the phase and amplitude information of the radio frequency harmonics. This information is extracted from the wave forms through fourier transformation by an array processor 78 (AP) (see FIG. 7E) for which purpose a Model DT7020 Array Processor circuit board, available from Data Translation, Inc., Marlboro, Mass. has been found satisfactory.

The fourier transformed wave forms are then displayed as phase and amplitude vs. frequency curves on the presentation screen of the personal computer 77 and constitute the end product of the fluorometer of this invention. The fourier transforms on the array processor are accomplished by using a commercial library of subroutines and other appropriate software in computer 77.

PULSED DYE LASER FLUOROMETER

While the CW fluorometer hereinabove described constitutes one embodiment of the present invention, in FIG. 8 a fluorometer employing a pulsed dye laser as the light source is illustrated in diagrammatic form corresponding to the showing of the CW laser fluorometer of FIG. 1. The fluorometer of FIG. 8 while functionally equivalent to the CW laser instrument described, is capable of higher frequency operation since the laser pulse harmonics extend into the gigahertz region of the spectrum.

Figure 8:
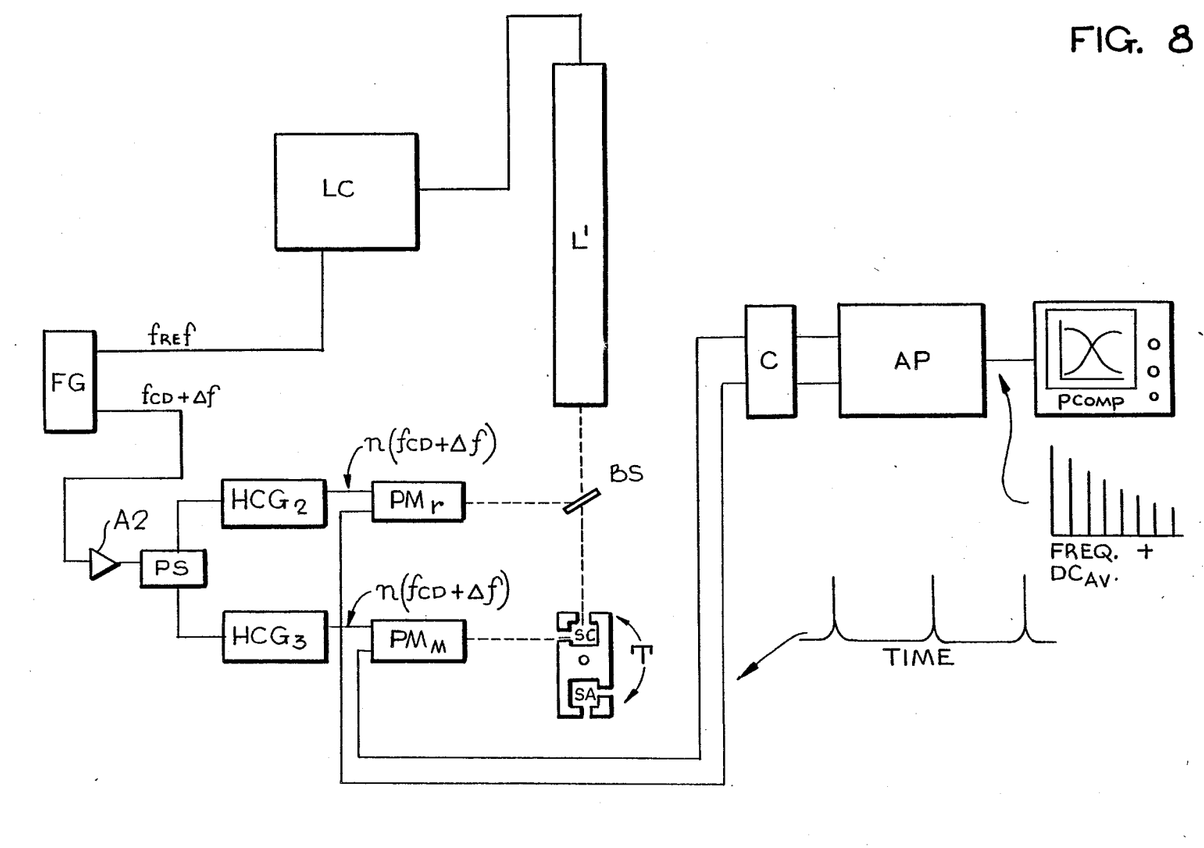
FIG. 8 is a schematic block diagram of a frequency domain fluorometer of this invention employing a pulsed dye laser light source.

As shown laser L' in the FIG. 8 embodiment is typically a synchronously pumped, cavity-dumped dye laser driven by a mode-locked, Argon-ion or Neodymium: YAG pump laser. Any intrinsically modulated coherent or incoherent light source may be used for L'. The frequency generator (FG) is phase locked to the laser pulsed repetition rate, either by supplying a reference frequency (fref) to the laser or being supplied with such a reference frequency from the mode-locking frequency generator in the laser control electronics (LC). The frequency generator (FG) also creates (fcd+$\Delta f$) a frequency equal to the laser cavity dumper repetition rate (fcd) plus a small offset ($\Delta f$), again 3 Hz. This frequency is amplified by ($A_2$) and split by power splitter (PS) to generate the cross-correlating combs produced by comb generators (HCG-2) and (HCG-3) to supply n(fcd+$\Delta f$) to the two photomultipliers (PMr) and (PMm) all as in the described FIG. 1 CW embodiment.

Measurement of the sample (SA) held in turret (T) as well as analysis and display is carried out in the same manner as in the aforedescribed CW laser instrument of FIG. 1.

The present major drawback of a pulsed dye laser fluorometer version of this invention resides in the relatively high cost of the laser light source as compared to the CW laser of the first described version. A further limitation of operating frequencies is encountered by the frequency response capability of currently available photomultiplier detectors.

Having described this invention it is believed that those familiar with the art will readily understand and appreciate that the preferred and modified embodiments thereof illustrated in the accompanying drawings and described above are susceptible to modification and substitution of equivalents without departing from the spirit and scope of the invention which is intended to be unlimited by the foregoing except as may appear in the following appended claims.

The embodiments of the invention in which an exclusive property or privilege is claimed are defined as follows:

1. In a cross-correlation, frequency domain spectrofluorometer operable to measure the phase and modulation response of a fluorescent sample, the combination comprising:
    means for producing amplitude modulated light having multiple, harmonically related, phase-locked, frequencies,
    means for exciting a fluorescent sample with said light to produce harmonically related, phase-locked, multiple frequency light emission signals;
    means for transforming said emission signals into low level frequency electrical detector signals having the modulation and phase characteristics of said multiple frequency emission signals, and
    means for simultaneously extracting the multi-harmonic phase and modulation data of the detector signals.

2. The combination of claim 1, wherein said light is produced by external harmonic modulation of a collimated coherent or incoherent DC light source.

3. The combination of claim 1, wherein said light is produced from intrinsically modulated laser pulse trains.

4. The combination of claim 1, and means for detecting said emission signals.

5. The combination of claim 1, and means for visually displaying said multi-harmonic phase and modulation data of said detector signals simultaneously in selected form.

6. The combination of claim 1, wherein said emission signals are high frequency light and said detector signals are relatively low frequency electrical signals.

7. The combination of claim 1, wherein said means for transforming said emission signals into said detector signals comprises a photomultiplier tube.

8. In a frequency domain fluorometer, the combination comprising: means for generating phase-locked ratio frequency signals containing a fundamental frequency and its integer harmonics; means for exciting a test sample with amplitude modulated light containing said fundamental frequency and integer harmonics to produce harmonically related, multiple frequency, phase-locked light signals; means for cross-correlating said light signals with said radio frequency signals simultaneously at said multiple, harmonically related, phase-locked frequencies to produce resultant cross-correlated signals having the same phase and modulation characteristics as said light signals; and means for simultaneously extracting and measuring the multi-harmonic phase and modulation responses of each frequency of the cross-correlated signals.

9. The combination of claim 8, and means for visually presenting said phase and modulation responses simultaneously in selected form.

10. The combination of claim 8, wherein the last named means thereof comprises means for digitizing said cross-correlated signals, and means for transforming the digitized data thereof into the frequency domain.

11. The combination of claim 10, wherein said means for transforming comprises an array processor operable to perform fourier transforms on said data.

12. The combination of claim 8, and means for generating said amplitude modulated light by external harmonic modulation of a coherent or incoherent D.C. light source.

13. In a frequency domain fluorometer, the combination comprising: means for providing amplitude modulated light containing multiple harmonically related phase-locked frequencies; means for exciting a test sample with said light to produce harmonically related, multiple frequency, phase-locked emission signals; means for detecting said emission signals, means for generating phase-locked, radio frequency signals containing a fundamental frequency and its integer harmonics, means for cross-correlating said emission signals with said radio frequency signals simultaneously at multiple harmonically related phase-locked frequencies to produce a resultant cross-correlated signal of like characteristics with said emission signals, and means for simultaneously extracting the phase and modulation data of each individual frequency of the multiple-frequency cross-correlated signal for analysis and simultaneously visual presentation of the sample's frequency response.

14. The combination of claim 13, wherein said means for generating said radio frequency signals and integer harmonics comprise a comb generator.

15. The combination of claim 13, and means for generating first and second sinusoidal R-F signals of different fundamental frequency, comb generator means receptive of said first R-F signal for producing said harmonically related, phase-locked frequencies, and means for extrinsically modulating a DC light source with said frequencies to effect said amplitude modulated light.

16. The combination of claim 15, and additional comb generator means receptive of said second R-F signal and productive of the integer harmonics of said second fundamental frequency; and said means for detecting said emission signals comprises a photomultiplier detector receptive of the signal output of said additional comb generator means.

17. A frequency domain spectrofluorometer comprising:
means for generating a pair of phase-coherent, sinusoidal signals of different fundamental frequency,
means for generating phase-coherent, multi-frequency integer harmonic signals from each of said fundamental frequency signals,
a source of collimated coherent or incoherent DC light,
means for extrinsically modulating said light with one of said multi-frequency harmonic signals to produce multi-frequency, phase-coherent amplitude modulated light signals,
means for exciting a fluorophore with said light signals to effect multi-frequency emission signals which are phase-coherent with said light signals;
means for simultaneously cross-correlating the harmonics of said emission signals and the harmonics of said other fundamental frequency signal to produce multi-frequency resultant signals having a repetition rate equal to the difference between the cross-correlated signals, and
means for simultaneously extracting the phase and modulation data for each frequency of said multi-frequency resultant signals.

18. A cross-correlation, frequency domain spectrofluorometer comprising:
means for generating a pair of phase-locked sinusoidal radio frequency signals of different fundamental frequency,
means for generating the integer harmonics of each of said fundamental frequency signals,
a source of collimated coherent or incoherent DC light,
means for modulating the intensity of said light with the harmonics of one of said pair of fundamental frequency signals to produce corresponding phase-coherent, multi-frequency, amplitude modulated light signals;
means for selectively exciting zero lifetime and fluorescent samples with said light signals to effect phase-coherent, multi-frequency emission signals therefrom;
photomultiplier detector means receptive of said emission and light signals,
means for cross-correlating said light and emission signals with the harmonics of said other of said fundamental frequency signals to produce beat note detector signals which have a repetition rate equal to the difference between the cross-correlated signal frequencies and contain the phase and modulation data for said other fundamental harmonic frequencies;
means for simultaneously extracting the phase and modulation data of each individual frequency of said detector signals; and
means for visually presenting said phase and modulation data simultaneously in selected form.

19. The combination of claim 18, wherein said source of light comprises a CW laser.

20. The combination of claim 18, wherein said source of light comprises an intrinsically modulated, coherent or incoherent light source.

21. A cross-correlation, frequency domain spectrofluorometer comprising:
   means for generating a pair of phase-locked sinusoidal radio frequency signals of different fundamental frequency,
   means for generating the integer harmonics of each of said fundamental frequency signals,
   a source of collimated coherent or incoherent DC light,
   means for modulating the intensity of said light with the harmonics of one of said pair of fundamental frequency signals to produce corresponding phase-coherent, multi-frequency, amplitude modulated light signals;
   means for selectively exciting zero lifetime and fluorescent samples with said light signals to effect phase-coherent, multi-frequency emission signals therefrom;
   means for transforming said high frequency emission signals into workable low level frequency detector signals while preserving the phase and modulation characteristics of said emission signals,
   means for simultaneously extracting the phase and modulation data of each individual frequency of said detector signals; and
   means for visually presenting said phase and modulation data simultaneously in selected form.

22. In a device for measuring the frequency response of a system comprising:
   means for generating two harmonic phase coherent, amplitude modulated, frequency combs, nf and $n(f+\Delta)$, respectively;
   first mixer means for providing a synchronizing, cross-correlated, reference frequency $N(\Delta)$ by mixing said two frequency combs, nf and $n(f+\Delta)$;
   means for supplying energy at frequency comb nf to the system,
   detector means for selectively detecting the input and output frequencies of the system,
   second mixer means for providing a cross-correlated, measurement frequency $N(\Delta)$ by mixing said output frequency and said frequency comb $n(f+\Delta)$, and
   means for acquiring, transforming, and analyzing said reference frequency and said measurement frequency to determine the system's frequency response.

* * * * *